US00PP11997P2

(12) United States Plant Patent
VandenBerg

(10) Patent No.: US PP11,997 P2
(45) Date of Patent: Jul. 17, 2001

(54) CHRYSANTHEMUM PLANT NAMED 'YOKODIAK'

(75) Inventor: Cornelis P. VandenBerg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/383,537

(22) Filed: Aug. 26, 1999

(51) Int. Cl.[7] ..... A01H 5/00
(52) U.S. Cl. ..... Plt./288
(58) Field of Search ..... Plt./288, 289, 287

*Primary Examiner*—Howard J. Locker
(74) *Attorney, Agent, or Firm*—C. A. Whealy

(57) ABSTRACT

A distinct cultivar of Chrysanthemum plant named 'Yokodiak', characterized by its upright, outwardly spreading and uniformly mounded plant habit; freely branching habit; strong, dark green foliage; uniform flowering; early flowering, eight-week response time; large decorative quilled-type inflorescences that are about 11.2 cm in diameter when produced as a disbud; initially light yellow becoming white-colored ray florets which gives a bi-colored appearance to the inflorescence; ray florets held upright; and excellent postproduction longevity with inflorescences and leaves maintaining good substance and color for about three or four weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Yokodiak.

The new Chrysanthemum is a product of a planned breeding program conducted by the Inventor in Salinas, Calif. The objective of the breeding program is to create new pot-type Chrysanthemum cultivars having desirable inflorescence forms and floret colors and good post-production longevity.

The new Chrysanthemum originated from a cross made by the Inventor in November, 1993, in Salinas, Calif., of a proprietary *Dendranthema grandiflora* seedling selection identified as code number YB-5775, as the female, or seed, parent, with a proprietary *Dendranthema grandiflora* seedling selection identified as code number YB-6145, as the male, or pollen, parent.

The new Chrysanthemum was discovered and selected by the Inventor as a flowering plant within the progeny of the stated cross in a controlled environment in Alva, Fla., in November, 1994. The selection of this plant was based on its desirable inflorescence form and floret colors and good post-production longevity.

Asexual reproduction of the new Chrysanthemum by terminal cuttings harvested in a controlled environment in Alva, Fla., has shown that the unique features of this new Chrysanthemum are stable and reproduced true to type in successive generations.

SUMMARY OF THE INVENTION

The cultivar Yokodiak has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yokodiak'. These characteristics in combination distinguish 'Yokodiak' as a new and distinct Chrysanthemum:

1. Upright, outwardly spreading and uniformly mounded plant habit.
2. Freely branching habit, full and dense plants.
3. Strong, dark green foliage.
4. Uniform flowering.
5. Early flowering, eight-week response time.
6. Can be produced as a disbudded or natural spray-type Chrysanthemum.
7. Large decorative quilled-type inflorescences that are about 11.2 cm in diameter when produced as a disbud.
8. Initially light yellow becoming white-colored ray florets which gives a bi-colored appearance to the inflorescence; ray florets held upright.
9. Excellent postproduction longevity with inflorescences and leaves maintaining good substance and color for about three or four weeks in an interior environment.

The new Chrysanthemum can be compared to the Chrysanthemum cultivar Phoenix, disclosed in U.S. Plant Pat. No. 8,843. However in side-by-side comparisons in Salinas, Calif., and Leamington, Ontario, Canada, under commercial practice, plants of the new Chrysanthemum differ from plants of the cultivar Phoenix in ray floret color and in the following characteristics:

1. Plants of the new Chrysanthemum are more vigorous than plants of the cultivar Phoenix.
2. Plants of the new Chrysanthemum are more outwardly spreading than plants of the cultivar Phoenix.
3. Plants of the new Chrysanthemum have larger inflorescences than plants of the cultivar Phoenix.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Yokodiak'.

The photograph at the bottom of the first sheet comprises a close-up view a typical inflorescence and upper (left) and lower (right) surfaces of typical leaves of the cultivar Yokodiak.

The photograph at the top of the second sheet comprises a side perspective view of typical flowering plants of 'Yokodiak' (left) and 'Phoenix' (right).

The photograph at the bottom of the second sheet comprises a close-up view of typical inflorescences of plants of 'Yokodiak' (left) and 'Phoenix' (right). Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Plants used for this description were grown as disbudded-types. Measurements and numerical values represent averages of typical flowering plants.

Botanical classification: *Dendranthema grandiflora* cultivar Yokodiak.

Commercial classification: Decorative quilled disbudded-type pot Chrysanthemum.

Parentage:

*Female or seed parent.*—Proprietary *Dendranthema grandiflora* seedling selection identified as YB-5775.

*Male or pollen parent.*—Proprietary *Dendranthema grandiflora* seedling selection identified as YB-6145.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Herbaceous decorative quilled pot Chrysanthemum which can be grown as a disbudded or as a natural spray-type. Inverted triangle; compact; upright and outwardly spreading giving a uniformly mounded appearance to the plant. Freely branching; about four lateral branches develop after removal of terminal apex (pinching); dense and full plants.

*Plant height.*—About 26 cm.

*Plant width.*—About 39 cm.

*Stem color.*—144A.

*Stem texture.*—Pubescent.

*Foliage description.*—Arrangement: Alternate. Length: About 6.8 cm. Width: About 5.6 cm. Apex: Cuspidate to mucronate. Base: Attenuate. Margin: Palmately lobed, sinuses between lateral lobes mostly divergent. Texture: Upper and lower surfaces with very fine pubescence; veins prominent on lower surface. Petiole length: About 2.5 cm. Color: Young foliage upper surface: 147A. Young foliage lower surface: 147B. Mature foliage upper surface: 147A. Mature foliage lower surface: 147B. Venation upper surface: 147B. Venation lower surface: 147B–147C.

Inflorescence description:

*Appearance.*—Decorative inflorescence form with quilled ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to three weeks of long day/short night conditions after planting followed by photoinductive short day/long night conditions flower about eight weeks later.

*Postproduction longevity.*—Inflorescences and leaves will maintain good color and substance for about three or four weeks in an interior environment.

*Quantity of Inflorescences.*—Freely flowering; about four inflorescences per lateral branch or about 16 inflorescences per plant.

*Inflorescence size.*—Diameter: About 11.2 cm. Depth (height): About 5.6 cm. Diameter of disc: About 2.5 mm, inconspicuous.

*Ray florets.*—Shape: Quilled. Orientation: Mostly upright, about 135° to peduncle. Aspect: Flat. Length: About 5.8 cm. Width: About 2.5 mm. Apex: Rounded. Margin: Entire. Texture: Satiny, smooth. Number of ray florets per inflorescence: About 171. Color: When opening: Light yellow, 5C. Fully opened, tube: White, 155D. Fully opened, throat: White, 155D.

*Disc florets.*—Shape: Tubular. Apex: Serrated. Length: About 7 mm. Width: Apex, about 2 mm; base, about 1 mm. Number of disc florets per inflorescence: Few, typically less than 20. Color: Immature: 154A. Mature: Apex: 9A. Mid-section: Light green. Base: White, 155D.

*Reproductive organs.*—Androecium: Present on disc florets only. Anther color: 9A. Pollen amount: Scarce. Pollen color: 14A. Gynoecium: Present on both ray and disc florets.

Disease resistance: Resistance to pathogens common to Chrysanthemums has not been observed on plants grown under commercial greenhouse conditions.

Seed production: Seed production has not been observed.

It is claimed:

1. A new and distinct cultivar of Chrysanthemum plant named 'Yokodiak', as illustrated and described.

* * * * *

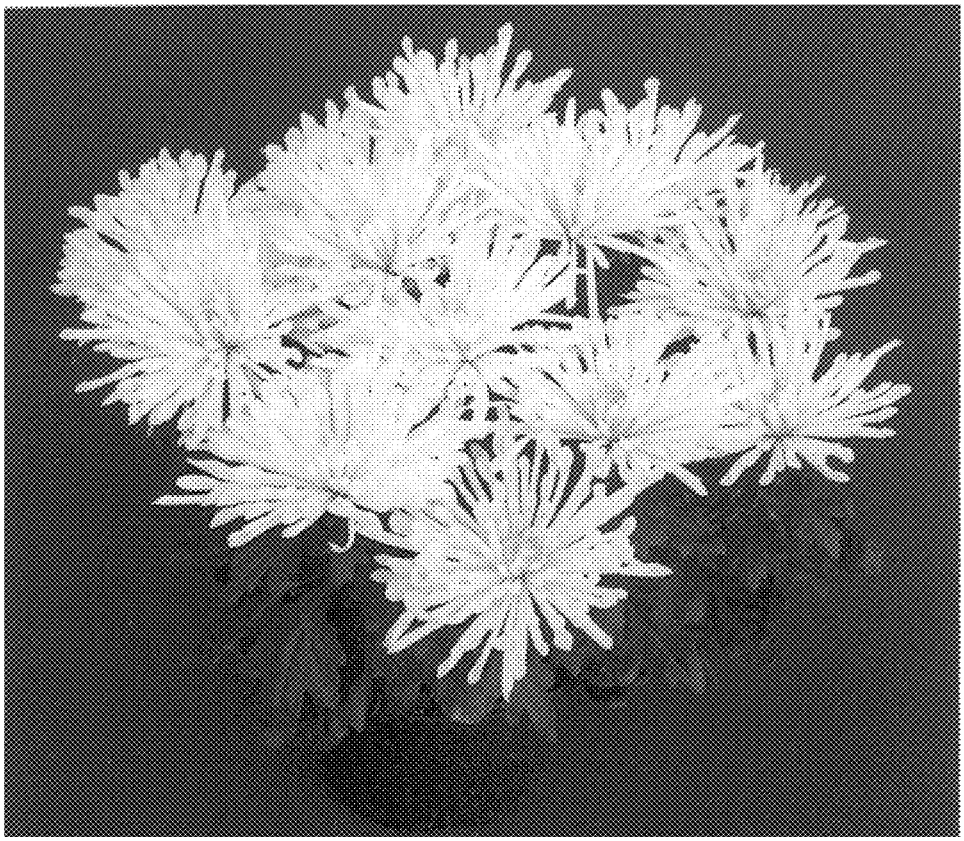
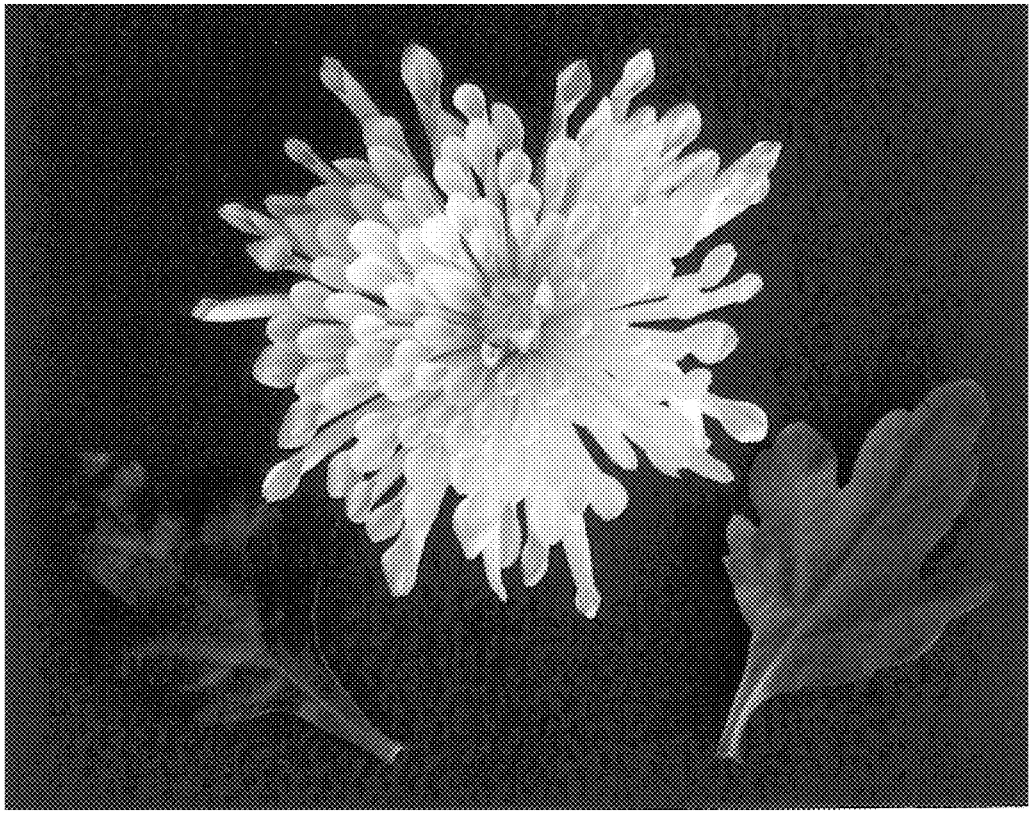

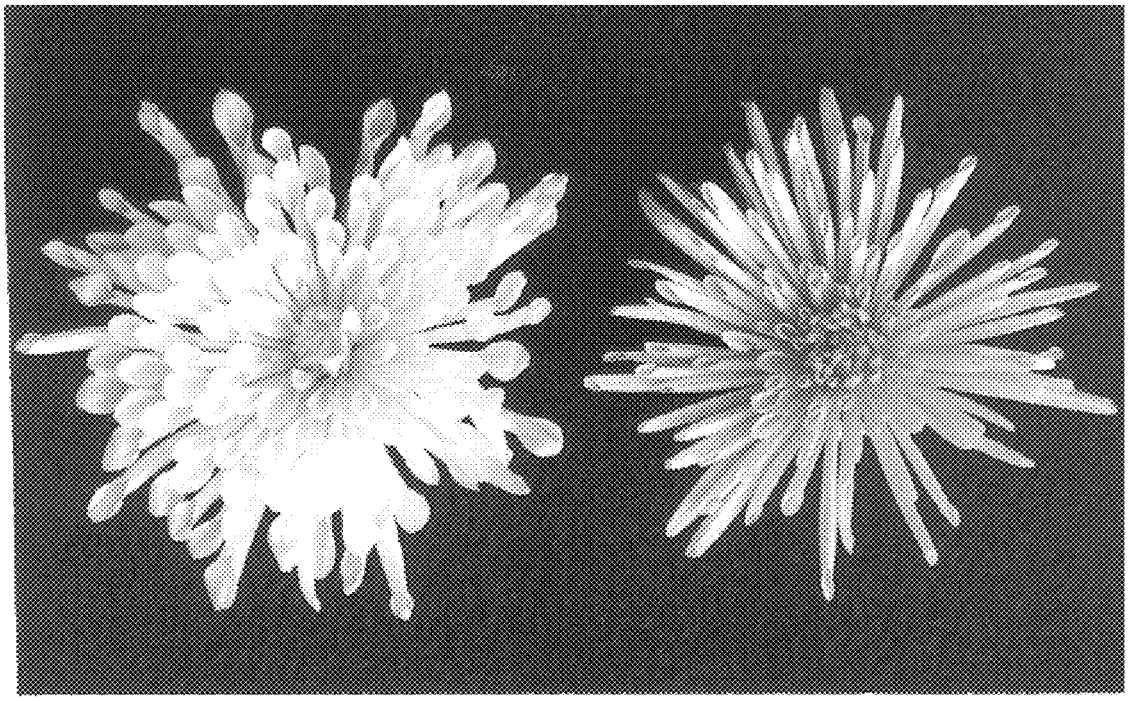

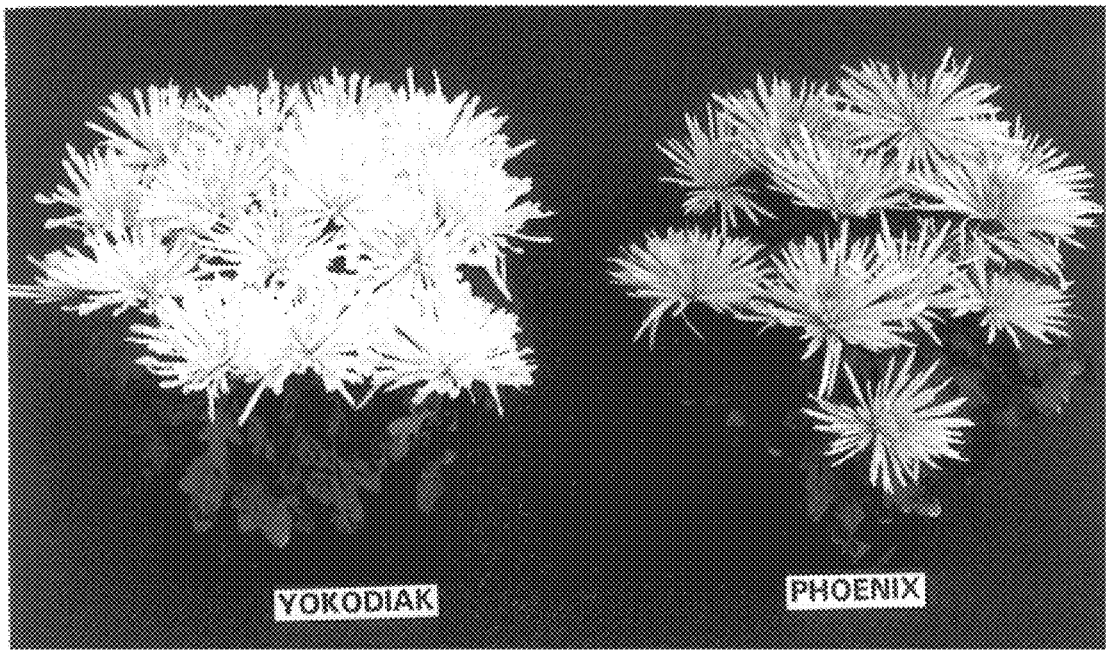
YOKODIAK
PHOENIX